(12) United States Patent
Bellini et al.

(10) Patent No.: US 7,683,038 B2
(45) Date of Patent: Mar. 23, 2010

(54) PERCARBOXYLATED POLYSACCHARIDES, AND A PROCESS FOR THEIR PREPARATION

(75) Inventors: Davide Bellini, Montegrotto Terme (IT); Vittorio Crescenzi, Rome (IT); Andrea Francescangeli, Rome (IT)

(73) Assignee: Fidia Farmaceutici S.p.A., Abano Terme (IT)

( * ) Notice: Subject to any disclaimer, the term of this patent is extended or adjusted under 35 U.S.C. 154(b) by 91 days.

(21) Appl. No.: 10/376,369

(22) Filed: Feb. 28, 2003

(65) Prior Publication Data

US 2003/0181689 A1 Sep. 25, 2003

Related U.S. Application Data

(63) Continuation-in-part of application No. PCT/EP01/10062, filed on Aug. 31, 2001.

(30) Foreign Application Priority Data

Aug. 31, 2000 (IT) .......................... PD2000A0208

(51) Int. Cl.
| | |
|---|---|
| *A61K 31/715* | (2006.01) |
| *A61K 31/70* | (2006.01) |
| *C07H 5/04* | (2006.01) |
| *C07H 5/06* | (2006.01) |
| *C08B 37/00* | (2006.01) |
| *C07H 13/00* | (2006.01) |
| *C07H 13/02* | (2006.01) |
| *C07H 23/00* | (2006.01) |
| *C08B 37/06* | (2006.01) |

(52) U.S. Cl. ............................ 514/53; 536/2; 536/18.7; 536/53; 536/55.2; 536/55.3; 536/117; 536/119; 536/121; 514/54; 514/62

(58) Field of Classification Search .................... 536/2, 536/18.7, 53, 55.2, 55.3, 114, 119, 121, 117; 514/53, 54, 62

See application file for complete search history.

(56) References Cited

U.S. PATENT DOCUMENTS

| | | | | |
|---|---|---|---|---|
| 4,746,504 | A * | 5/1988 | Nimrod et al. | 424/1.73 |
| 6,222,031 | B1 * | 4/2001 | Wakabayashi et al. | 536/124 |
| 6,579,978 | B1 * | 6/2003 | Renier et al. | 536/53 |
| 6,586,588 | B1 * | 7/2003 | Cimecioglu et al. | 536/104 |
| 2003/0073663 | A1 * | 4/2003 | Wiseman et al. | 514/54 |

FOREIGN PATENT DOCUMENTS

| | | |
|---|---|---|
| WO | WO 96 38484 A | 12/1996 |
| WO | WO 98 45335 | 10/1998 |
| WO | WO 00/01733 A1 * | 1/2000 |

OTHER PUBLICATIONS

Jiang et al, "Study on TEMPO-Mediated Selective Oxidation of Hyaluronan and the Effects of Salt on the Reaction Kinetics", Carbohydrate Reearch, (Aug. 7, 2000), vol. 327, pp. 455-461.*

Database Chemical Abstract, Chemical Abstracts Service, Columbus OH, Accession No. 135:346080. XP002189577, 2000, and Lanzetta et al., "Use of Carbohydrates in Tanning Technology," Cuolo, Pelli, Materle Concianti 76:325-334, 2000.

de Nooy et al., "Synthesis and Preliminary Characterisation of Charged Derivatives and Hydrogels from Scleroglucan," Carbohydrate Research 324:116-126, 2000.

de Nooy et al., "Selective Oxidation of Primary Alcohol Groups in Polysaccharides," pp. 1-99.

de Nooy et al., "Selective Oxidation of Primary Alcohols Mediated by Nitroxyl Radical in Aqueous Solution. Kinetics and Mechanism," Tetrahedron 51:8023-8032, 1995.

de Nooy et al., "TEMPO-Mediated Oxidation of Pullulan and Influence of Ionic Strength and Linear Charge Density on the Dimensions of the Obtained Polyelectrolyte Chains," Macromolecules 29:6541-6547, 1996.

* cited by examiner

*Primary Examiner*—Shaojia Anna Jiang
*Assistant Examiner*—Everett White
(74) *Attorney, Agent, or Firm*—Clark & Elbing LLP

(57) ABSTRACT

The present invention relates to percarboxylated polysaccharide selected from the group consisting of gellan, carboxymethylcellulose, pectic acid, pectin and hyaluronic acid derivatives; the process for their preparation and their use in the pharmaceutical, biomedical, surgical and healthcare fields.

16 Claims, 2 Drawing Sheets

PERCARBOXYLATED POLYSACCHARIDES, AND A PROCESS FOR THEIR PREPARATION

CROSS REFERENCE TO RELATED APPLICATIONS

This application is a continuation-in-part of International Application PCT/EP01/10062, filed Aug. 31, 2001, which was published in English under PCT Article 21(2) and claims priority from Italian application no. PD2000A000208, filed Aug. 31, 2000.

FIELD OF THE INVENTION

The present invention describes percarboxylated polysaccharides, the process for their preparation and their use in the pharmaceutical field and in the preparation of biomaterials for surgical, biomedical and healthcare uses.

STATE OF THE ART

Hyaluronic acid is a heteropolysaccharide composed of alternating residues of D-glucuronic acid and N-acetylglucosamine. It is a polymer with a linear chain and a molecular weight that may vary between 50,000 and 13,000,000 Da, according to the source from which it is obtained and the methods used to prepare it.

It is present in nature in the pericellular gels, in the fundamental substance of the connective tissue of vertebrate organisms, of which it represents one of the main components, in the synovial fluid of joints, in the vitreous humor, in the tissues of human umbilical cords and in cockscombs.

In recent years, various polysaccharides, not carboxylated by oxidation of the primary hydroxyls, have been modified by the use of a selective reagent, specific to primary alcohol groups, namely 2,2,6,6-tetramethyl-1-piperidinyloxy (TEMPO). The modification of non-carboxylated polysaccharides such as pullulan (De Nooy A. E. J. et al., *Macromolecules* 1996, 29, 6541-6547) methyl-α-D-glycopyranoside (De Nooy A. E. J. et al., *Tetrahedron* 1995, 51, 8023-8032), scleroglucan (De Nooy A. E. J. et al., *Carbohydrate Research* 2000, 324, 116-126), have been described in a publication entitled "Selective oxidation of primary alcohol groups in polysaccharides" (1997) by De Nooy A. E. J., which reports various oxidation processes both on non-carboxylated polysaccharides and, more generally, on hydroxy groups of alcohols of a different nature. However, although the TEMPO-mediated oxydation of hyaluronic acid is known to the state of the art (Bo Jiang et al., *Carbohyd. Res.* 2000; vol. 327, pages 455-61), there is no report in the art on the application of such reaction on carboxylated polysaccharides. Concerning this, it is worthy to note that Jiang et al. themselves affirmed in the above document that the TEMPO-mediated oxidation is a rather complex process, and consequently the presence of other groups on the hyaluronic chain, as occurs for hyaluronic acid derivatives, may also have unforeseeable repercussion on the reaction. Moreover, following to the reaction a substantial degradation of the polymer occurred, that is caused, according to Jang et al., by the oxidation process itself.

The introduction of additional carboxy groups in the hyaluronic chain increases the stability of the derivatives (increase in the percentage of esterification, amidation, cross-linking, etc.), their viscosity, their hydrophilic properties (the greater the number of carboxylate groups, the greater their solubility in water and in aprotic solvents, such as DMSO), and their hydrophobic properties (the introduction of additional carboxy groups makes it possible to introduce lipid molecules, such as long-chain fatty acids, by esterification or amidation).

SUMMARY OF THE INVENTION

The present invention relates to "percarboxylated" hyaluronic acid derivatives, comprising at least one repeating unit of formula (I):

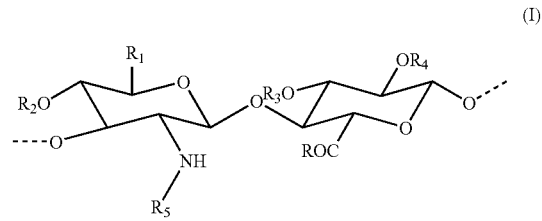

(I)

wherein
R is OH, O⁻, an alcoholic or an amino group of the aliphatic, aromatic, arylaliphatic, cycloaliphatic and heterocyclic series;
$R_1$ is $COR_6$, wherein $R_6$ is OH, O⁻, an alcoholic or an amino group of the aliphatic, aromatic, arylaliphatic, cycloaliphatic and heterocyclic series; an alcoholic group of hyaluronic acid, or an amino group of N-deacetylated hyaluronic acid;
$R_2$, $R_3$, $R_4$, equal or different from each other, are H, $SO_3^-$, an acyl group deriving from a carboxylic acid of the aliphatic, aromatic, arylaliphatic, cycloaliphatic, heterocyclic series; or a residue of hemiester of succinic acid or of heavy metal salts of hemiester of succinic acid;
$R_5$ is $COCH_3$, H, $SO_3^-$, an acyl group deriving from a carboxylic acid of the aliphatic, aromatic, arylaliphatic, cycloaliphatic, heterocyclic series, or an acyl group of hyaluronic acid;
provided that, when R is OH, $R_5$ is $COCH_3$ and $R_2=R_3=R_4=H$, $R_6$ is different from OH and O⁻.

Further subject of the invention are "percarboxylated" polysaccharides selected from the group consisting of gellan, carboxymethylcellulose, pectin and pectic acid.

The present invention also relates to the process for their preparation and the numerous applications of such products in the pharmaceutical, biomedical, surgical and healthcare fields.

DETAILED DESCRIPTION OF THE INVENTION

Figure 1:
FIG. 1 shows a Scanning Electron Micrograph (SEM) of a membrane made of HYAFF® 11 coming from not-percarboxylated hyaluronic acid (benzyl ester of hyaluronic acid having an esterification degree of 100%).

The term "percarboxylated", as used herein, means that all or part of the primary hydroxyl groups present on the polymer have been replaced by carboxy groups, and modifications thereof, by an oxidation process.

The term "percarboxylation degree" as used herein, means the percentage of carboxy groups, or modifications thereof, introduced by an oxidation process.

According to the invention, the percarboxylation degree of the present derivatives is comprised between 1% and 100%, and preferably between 25% and 75%.

The present invention relates to new "percarboxylated" polysaccharides selected from the hyaluronic acid derivatives of formula (I) above reported, gellan, pectin and pectic acid.

Of the percarboxylated derivatives of hyaluronic acid according to the present invention, the following are to be preferred:

the hyaluronic acid esters wherein a part or all of the carboxy functions, including those obtained by oxydation of the primary hydroxyls, are esterified with alcohols of the aliphatic, aromatic, arylaliphatic, cycloaliphatic, heterocyclic series, as disclosed in EP 0216453 B1, which we incorporate herewith by reference;

the autocross-linked esters of hyaluronic acid wherein part or all of the carboxy functions, including those obtained by oxydation of the primary hydroxyls, are esterified with the alcohol functions of the same polysaccharide chain or other chains, as disclosed in EP 0341745 B1, which we incorporate herewith by reference;

the cross-linked esters of hyaluronic acid wherein part or all of the carboxy functions, including those obtained by oxydation of the primary hydroxyls, are esterified with polyalcohols of the aliphatic, aromatic, arylaliphatic, cycloaliphatic, heterocyclic series, generating cross-linking by means of spacer chains, as disclosed in EP 0265116 B1, which we incorporate herewith by reference;

the hemiesters of succinic acid or the heavy metal salts of the hemiester of succinic acid with hyaluronic acid or with partial or total esters of hyaluronic acid, like those disclosed in WO 96/357207, which we incorporate herewith by reference;

the O-sulphated derivatives, as disclosed in WO95/25751, which we incorporate herewith by reference, or N-sulphated derivatives, as disclosed in WO98/45335, which we incorporate herewith by reference;

the amides of hyaluronic acid, like those disclosed in WO00/01733, which we incorporate herewith by reference.

Preferred are the benzyl ester of hyaluronic acid having a percarboxylation degree of 25%, the zinc salt of hyaluronic acid having a percarboxylation degree of 25% and the autocross-linked hyaluronic acid (ACP) having a percarboxylation degree of 50%.

When not otherwise specified, the terms aliphatic, aromatic, arylaliphatic, cycloaliphatic and heterocyclic, as used herein, should be intended as follows:

"aliphatic" means acyclic or pertaining to open-chain or branched carbon compounds such as alkanes, alkenes or alkynes. Examples of an aliphatic moiety include but are not limited to C1-C20 noncyclic hydrocarbons and their isomers such as methyl, ethyl, propyl, isopropyl, n-butyl, tert-butyl, pentyl, isopentyl, neopentyl, tert-pentyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,2-ethylbutyl, 2-ethylbutyl, 1,1,2-trimethylpropyl, heptyl, octyl, nonyl, decyl, undecyl, dodecyl, tridecyl, tetradecyl, pentadecyl, hexadecyl, cetyl, heptadecyl, octadecyl, nonadecyl, stearyl, etc.

"aromatic" means an aryl moiety having one or more unsaturated rings, each ring usually having 5 to 8 members and preferably 5 to 6 members. Examples of the aromatic moiety include but are not limited to benzyl, toluyl, naphalyl, anthracenyl, phenantryl, fluorenyl, coronenyl, triphenylenyl, fluoranthenyl, benzofluoranthenyl, benzopyrenyl and pyrenyl.

"cycloaliphatic" indicates a carbon ring structure, usually having 3 to 8 members and preferably 5 to 6 members, that does not contain a resonance structure. Examples of cycloaliphatic groups include but are not limited to cycloalkanes and cycloolefins such as cyclopropyl, cyclobutyl, cyclopentyl, cyclohexyl, cycloheptyl, cyclooctyl, cyclohexenyl (tetrahydrobenzenyl), cyclohexylidenyl, and cyclooctadienyl.

"heterocyclic" relates to dissimilar atoms in a ring. A heterocyclic group is a heteroaryl group usually having a 3- to 8-membered, preferably 5- to 6-membered ring or fused ring containing at least one hetero atom (such as O, S, N, etc.) and include but are not limited to thienyl, furanyl, pyranyl, 2H-pyrrolyl, imidazolyl, pyrazolyl, pyridyl, pyrazinyl, pyrimidyl, pyridazinyl, isothiazolyl, isoxazolyl, furazanyl, benzothienyl, isobenzofuranyl, chromenyl, indolindinyl, isoindolyl, indolyl, purinyl, quinolidinyl, isoquinolyl, quinolyl, phtalazinyl, quinazolyl, carbazolyl, acridinyl, and phenanthridinyl.

"arylaliphatic" means a group having both aromatic and aliphatic substituents as defined above. Examples of arylalkyl groups include but are not limited to ethylbenzenyl, isobutylbenzeneyl, benzyl, ethylbenzyl, propylbenzyl, isopropylbenzyl, butylbenzyl, isobutylbenzyl, cyclohexylbenzyl, styrenyl, and biphenyl.

Percarboxylated hyaluronic acid derivatives can be used for the preparation of pharmaceutical compositions, for example in the form of gels, for the transport and release of drugs and biologically active substances to be used in viscoelastic surgery or ophthalmic surgery.

The present percarboxylated derivatives can also by salified with heavy metals wherein the heavy metals are the elements of the $4^{th}$, $5^{th}$ or $6^{th}$ period of the periodic table, such as silver, iron, cobalt, copper, zinc, arsenic, strontium, zirconium, antimony, gold, cesium, tungsten, selenium and platinum, ruthenium, bismuth, tin, titanium, gallium, mercury.

These salts can be used in dermatology, ophthalmology, dentistry, rheumatology, urology, gynaecology, internal surgery, as food supplements, antioxidants, antirheumatic and anticancer agents, antiinflammatories, analgesics and antiulcer agents.

Also the salts of the present percarboxylated derivatives may be prepared with pharmacologically and/or biologically active substances.

Of the pharmacologically active substances, the following are preferred:

antibiotics, anti-infective, antimicrobial, antifungal, antiviral, cytostatic, cytotoxic, anticancer, anti-inflammatory, wound-healing agents, anaesthetics, analgesics, vasoconstrictors, cholinergic or adrenergic agonists and antagonists, antithrombotics, anticoagulants, haemostatic, fibrinolytic, thrombolytic agents.

As biologically active substances should be intended for example proteins and their fragments, peptides, polynucleotides, growth factors, enzymes, vaccines, or substances used in the treatment of diseases associated with genetic defects, such as those that are caused by enzymatic hypo- or hyperactivity due to defects of the gene that codes for a given enzyme, or deforming or hereditary diseases.

The present percarboxylated derivatives can also be used in association with radioactive and non-radioactive substances used in contrast systems, and as tracers in in vivo diagnostics for the identification and cure of cancer tissues or damaged tissues.

A considerable advantage is represented by the possibility of processing the compounds of the present invention and their salts in various forms of biomaterials such as sponges, films, membranes, threads, tampons, non-woven tissues, felts, microspheres, nanospheres, gauze pads, gels, guide channels, and associations thereof.

Figure 2:
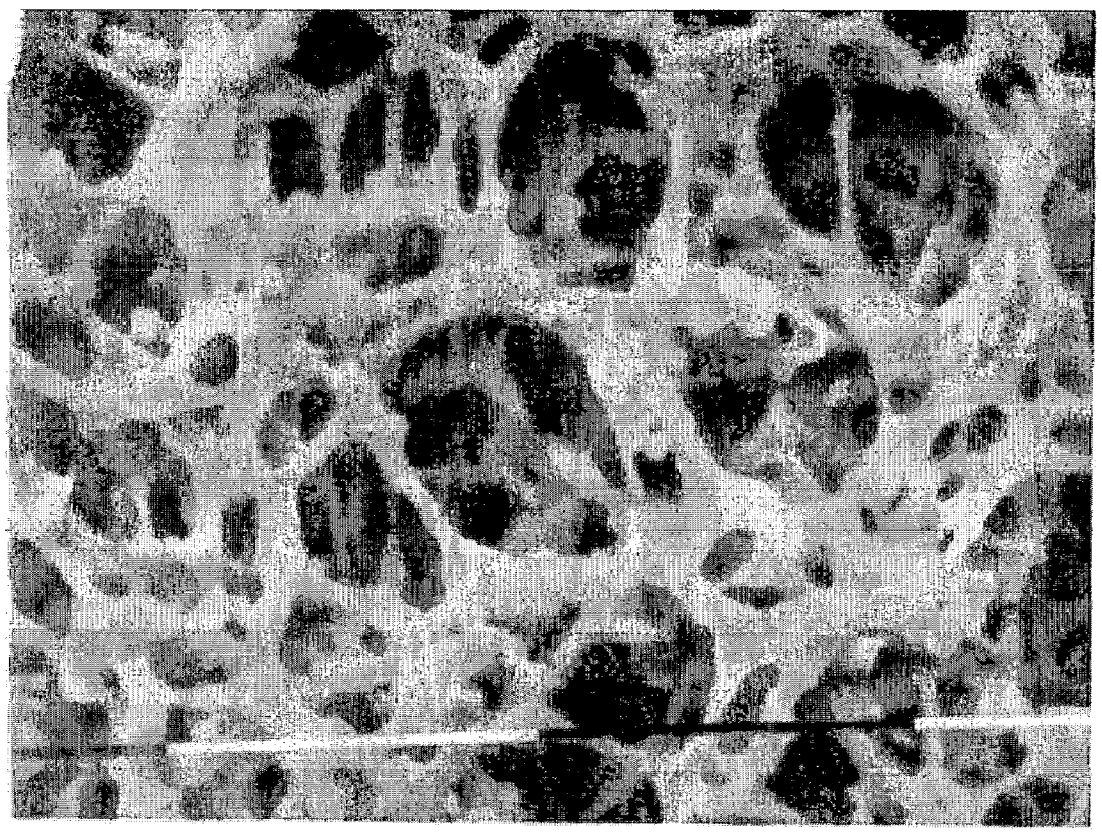
FIG. 2 shows a SEM of a membrane made of HYAFF® 11 coming from percarboxylated hyaluronic acid according to the invention (benzyl ester of hyaluronic acid having a percarboxylation degree of 50% and an esterification degree of 150%).

FIG. 2 shows the SEM image of a membrane made of "percarboxylated" HYAFF® 11 according to the invention (benzyl ester of hyaluronic acid having a percarboxylation degree of 50% and an esterification degree of 150%). By comparing this membrane with that showed in FIG. 1 containing not-percarboxylated HYAFF® 11 having an esterification degree of 100%, it is evident that the surface of the membrane made of the percarboxylated material is completely different from the other, due to the increase in hydrophobicity of the present material, and shows a different surface porosity.

The porosity of the "percarboxylated" membrane in FIG. 2 allows new uses and applications.

These biomaterials may be constituted by one or more of the present percarboxylated derivatives, optionally in association with natural, synthetic, semisynthetic polymers and, optionally, further being in combination with pharmacologically and/or biologically active substances.

Examples of the natural polymers that can be used are collagen, coprecipitates of collagen and glycosaminoglycans, cellulose, polysaccharides in the form of gels such as chitin, chitosan, pectin and pectic acid, agar, agarose, xanthane, gellan, alginic acid or the alginates, polymannan or polyglycans, starch, natural gums.

Examples of semisynthetic polymers of possible use are collagen cross-linked with agents such as aldehydes or precursors of the same, dicarboxylic acids or their halides, diamine, derivatives of cellulose, hyaluronic acid, chitin or chitosan, xanthane, pectin or pectic acid, polyglycans, polymannan, agar, agarose, natural gums and glycosaminoglycans.

Synthetic polymer can be chosen, for example, from the group consisting of polylactic acid, polyglycolic acid or the derivatives thereof, polydioxanes, polyphosphazenes, polysulphonic resins, polyurethanes, PTFE.

The above-said biomaterials can be used in various surgical fields, for example in internal surgery, osteo-articular surgery, neurosurgery, anastomotic, viscoelastic, ophthalmic, oncological, plastic-aesthetic, otolaryngological, abdominal-pelvic, urogynaecological, cardiovascular surgery, in the prevention of post-surgical adhesions and hypertrophic scars.

Moreover, they can be used in blood dialysis and in other branches of medicine such as cardiology, angiology, dermatology, ophthalmology, otolaryngology, dentistry, orthopaedics, gynaecology, urology, in extracorporeal circulation and oxygenation and in cosmetics.

Said biomaterials, in their various forms, are particularly suitable for use as scaffolds for the growth of cells such as mesenchymal or mature cells to obtain connective, bone, glandular, nervous, muscular, hepatic tissue etc.

The biomaterials comprising the present percarboxylated derivatives can be used, in association with biologically and/or pharmacologically active substances, as vehicling agents for the preparation of slow release pharmaceutical compositions; moreover, the present percarboxylated derivatives can be used as the active ingredients, in combination with pharmaceutically acceptable excipients and/or diluents, for the preparation of pharmaceutical compositions.

The derivatives thus obtained can also be used in the processes of coating objects used both in the medical field and in other sectors of industry, providing new biological characteristics to the surfaces of the materials used as supports.

The objects that can be thus coated are, for example, catheters, guide channels, probes, cardiac valves, soft tissue replacements, replacements of animal origin, artificial tendons, bone and cardiovascular replacements, contact lenses, blood oxygenators, artificial kidneys, hearts, pancreas and livers, blood bags, syringes, surgical instruments, filtration systems, laboratory instruments, containers for cell and tissue culture and regeneration, supports for peptides, proteins and antibodies.

The process of coating the surfaces of such objects can be performed by the Plasma Coating technique, as described in the international patent application by the Applicant, No. WO96/24392.

The present percarboxylated derivatives can be obtained by an oxidation process, that acts selectively on the primary hydroxyl groups, for example by reaction of the polisaccharide, selected from hyaluronic acid and derivatives thereof, gellan, pectic acid and pectin, with sodium hypochlorite in aqueous solution at a low temperature, preferably ranging between 0° C. and −1° C., and in the presence of 2,2,6,6-tetramethyl-1-piperidinyloxy (TEMPO). The degree of percarboxylation deriving therefrom, depends on the quantity of the oxidising agent (hypochlorite) used in the reaction.

Also when the starting polysaccharide is a hyaluronic acid derivative, the present process has lead to the desired percarboxylated products, without showing the drawbacks expected, and in particular the substantial degradation of the polymer disclosed by Bo Jiang et al.

The process for the preparation of percarboxylated hyaluronic acid derivatives wherein $R_6$ is different from OH or O−, comprises the following steps:

a) selective oxidation of part or all primary hydroxyl groups of the starting hyaluronic acid derivatives;

b) preparation of the quaternary ammonium salt, preferably the tetrabutylammonium salt, of the percarboxylated hyaluronic acid derivative coming from step a);

c) reaction of the said quaternary ammonium salt coming from step b) with different reagents depending on which is the derivative desired. In particular, the quaternary ammonium salt is reacted with a sulphating agent to obtain the O-sulphated or N-sulphated derivatives, with chloromethylpyridinium iodide to obtain the autocross-linked derivatives, with succinic anhydride to obtain the hemiesters of succinic acid, etc., as disclosed in the above patent documents, herewith incorporated by reference.

The following examples are given to provide non-limiting illustrations of the present invention.

EXAMPLE 1

Preparation of percarboxylated hyaluronic acid in the form of a sodium salt with 25% percarboxylation 1 g of sodium hyaluronate (2.5 mmole) with a mean molecular weight of 200 KDa is solubilised in 50 ml of water. The solution is cooled in a bath with a thermostat set at −1° C., and is then supplemented with 40 mg (0.26 mmole) of TEMPO and 260 mg (2.5 mmole) of NaBr (sodium bromide).

A solution of 15% sodium hypochlorite is added in a quantity of 0.3 ml, equal to 0.625 mmole, corresponding to 25% of the moles of sodium hyaluronate present. The solution is mixed and the pH maintained at 9-9.2 by the addition of a solution of 0.5 M NaOH. Some minutes later, the pH remains stable with no further additions of this kind. A volume of absolute ethanol equal to 5 ml is added and the solution is neutralised by adding 1 M HCl until the pH reaches 6.9-7.2. Then 95 mg (2.5 mmoles) of sodium borohydride is added and the mixture is agitated overnight at room temperature. The solution is neutralised to pH 6 and precipitated with acetone.

The product thus obtained is characterised analytically to determine the percentage of carboxylation.

Yield of the reaction: 95%.

Percentage of percarboxylation (acidimetric): 25%.

EXAMPLE 2

Preparation of percarboxylated hyaluronic acid in the form of a sodium salt with 50% percarboxylation 1 g of sodium hyaluronate (2.5 mmoles) with a mean molecular weight of 200 KDa is solubilised in 50 ml of water. The solution is cooled in a bath with a thermostat set at $-1°$ C., and is then supplemented with 40 mg (0.26 mmole) of TEMPO and 260 mg (2.5 mmole) of NaBr (sodium bromide). A solution of 15% sodium hypochlorite is added in a quantity of 0.6 ml, equal to 1.25 mmole, corresponding to 50% of the moles of sodium hyaluronate present. The solution is mixed and the pH maintained at 9-9.2 by the addition of a solution of 0.1 M NaOH. Some minutes later, the pH remains stable with no further additions of this kind. A volume of absolute ethanol equal to 5 ml is added and the solution is neutralised by adding 1 M HCl until the pH reaches 6.9-7.2. Then 95 mg (2.5 mmoles) of sodium borohydride is added and the mixture is agitated overnight at room temperature.

The solution is neutralised to pH 6 and precipitated with acetone.

The product thus obtained is characterised analytically to determine the percentage of carboxylation.

Yield of the reaction: 95%.

Percentage of percarboxylation (acidimetric): 50%.

EXAMPLE 3

Preparation of percarboxylated hyaluronic acid in the form of a sodium salt with 75% percarboxylation 1 g of sodium hyaluronate (2.5 mmoles) with a mean molecular weight of 200 KDa is solubilised in 50 ml of water. The solution is cooled in a bath with a thermostat set at $-1°$ C., and is then supplemented with 40 mg (0.26 mmole) of TEMPO and 260 mg (2.5 mmole) of NaBr (sodium bromide). A solution of 15% sodium hypochlorite is added in a quantity of 0.9 ml, equal to 1.875 mmole, corresponding to 75% of the moles of sodium hyaluronate present. The solution is mixed and the pH maintained at 9-9.2 by the addition of a solution of 0.5 M NaOH. Some minutes later, the pH remains stable with no further additions of this kind. A volume of absolute ethanol equal to 5 ml is added and the solution is neutralised by adding 1 M HCl until the pH reaches 6.9-7.2. Then 95 mg (2.5 mmoles) of sodium borohydride is added and the mixture is agitated overnight at room temperature.

The solution is neutralised to pH 6 and precipitated with acetone.

The product thus obtained is characterised analytically to determine the percentage of carboxylation.

Yield of the reaction: 95%.

Percentage of percarboxylation (acidimetric): 75%.

EXAMPLE 4

Preparation of percarboxylated gellan in the form of a sodium salt with 50% percarboxylation 2 g of gellan sodium salt (2.95 mmoles) with a mean molecular weight of 700 KDa is solubilised in 100 ml of water. The solution is cooled in a bath with a thermostat set at $-1°$ C., and is then supplemented with 40 mg (0.26 mmole) of TEMPO and 300 mg (2.9 mmole) of NaBr (sodium bromide). A solution of 15% sodium hypochlorite is added in a quantity of 0.705 ml, equal to 1.47 mmole, corresponding to 50% of the moles of gellan sodium salt present. The solution is mixed and the pH maintained at 9-9.2 by the addition of a solution of 0.5 M NaOH. Some minutes later, the pH remains stable with no further additions of this kind. A volume of absolute ethanol equal to 5 ml is added and the solution is neutralised by adding 1 M HCl until the pH reaches 6.9-7.2. Then 110 mg (2.9 mmoles) of sodium borohydride is added and the mixture is agitated overnight at room temperature. The solution is neutralised to pH 6 and precipitated with acetone.

The product thus obtained is characterised analytically to determine the percentage of carboxylation.

Yield of the reaction: 95%.

Percentage of percarboxylation (acidimetric): 50%.

EXAMPLE 5

Preparation of a benzyl ester (HYAFF®11) from hyaluronic acid with 25% percarboxylation 6.34 g (10 mmoles) of tetrabutylammonium salt of percarboxylated hyaluronic acid according to example 1 is solubilised in 250 ml of dimethylsulphoxide (DMSO) at room temperature. To this solution is added 1187 ml of benzyl bromide (10 mmoles) and the solution is kept at a temperature of 30° C. for 24 hours. A solution of 2.5% (w/w) NaCl in water is then added and the resulting mixture is poured into 750 ml of acetone, while agitating. A precipitate is formed that is filtered and washed three times in 100 ml of acetone/water (ratio 5:1), three times in 100 ml of acetone, and then vacuum-dried for 24 hours at 30° C. Thus, 4.25 g of the desired product are obtained with 125% of total benzylic esterification (it should be intended that all the carboxy groups of the polymer not percarboxylated, and all the carboxy groups coming from percarboxylation are esterified). Quantitative determination of the benzylic alcohol content is conducted by gas chromatography after alkaline hydrolysis. The total content of ester groups is determined according to the saponification method described on pages 169-172 of "Quantitative organic analysis via functional groups', IV Ed., John Wiley and Sons Publication.

EXAMPLE 6

Preparation of cross-linked hyaluronic acid (ACP) from hyaluronic acid with 50% percarboxylation 6.5 g (10 mmoles) of tetrabutylammonium salt of percarboxylated hyaluronic acid according to example 2 is solubilised in 260 ml of N-methyl-2-pirrolidone (NMP) at room temperature. To this solution is added 1.4 ml of triethylamine (10 mmoles) and the resulting solution is agitated for 30 minutes. To this solution is added 0.766 mg of 2-chloro-1-methyl-pyridinium iodide equal to 30% of the initial moles of percarboxylated hyaluronic acid dissolved in 5 ml of NMP. The solution is agitated for 4 hours at room temperature. A saline solution of 2.5% NaCl in water (w/w) is then added. The mixture obtained is slowly poured into 750 ml of acetone while under constant agitation. A precipitate is formed that is filtered and washed three times in 100 ml of acetone/water (ratio 5:1) and three times with 100 ml of acetone, and then vacuum-dried for 24 hours at 30° C. Thus, 3.9 g of the desired product are obtained equal to 30% cross-linking. The total content of ester groups is determined according to the saponification method described on pages 169-172 of "Quantitative organic analysis via functional groups", IV Ed., John Wiley and Sons Publication.

EXAMPLE 7

Preparation of a zinc salt of hyaluronic acid with 25% percarboxylation 2 g of tetrabutylammonium salt of percarboxylated hyaluronic acid according to Example 1 is solubilised in 100 ml of a 5% (w/w) solution of zinc chloride ($ZnCl_2$) in water. The solution is agitated for 15 hours at room temperature. In order to eliminate the excess salts, the solution is dialysed through dialysis membranes until all the residue salts (chlorides) have disappeared. To demonstrate the absence of salts from the dialysed solution, it is tested with a 0.1 molar solution of silver nitrate in water. If the dialysed solution does not become cloudy on contact with the silver nitrate solution, this indicates that no chloride residues are present. The salt-free, dialysed solution is freeze-dried and analysed for its zinc content. The zinc content proves to be 10% bivalent zinc ($Zn^{2+}$), vs the theoretical content of 7.95. The resulting percentage perfectly reflects the value of percarboxylation of the hyaluronic acid used.

EXAMPLE 8

Preparation of films using percarboxylated hyaluronic acid esters (HYAFF®)

A solution equal to 100 mg/ml of the percarboxylated derivative in dimethylsulphoxide (DMSO) according to Example 5 is prepared by dissolving 1 g of benzyl ester at 125% in 10 ml of DMSO. A thin layer of solution is spread over a glass plate, taking care to create a layer that is 10 times thicker than the desired thickness of the final film. The glass plate is immersed in a bath of ethanol that absorbs the DMSO but does not solubilise the percarboxylated hyaluronic acid ester, which solidifies. The film is detached from the glass plate and washed repeatedly with water and again with ethanol. The film thus obtained is dried in a press for 24 hours at 30° C.

EXAMPLE 9

Preparation of 75% percarboxylated hyaluronic acid, starting from an ester derivative of hyaluronic acid with 5% esterified benzyl alcohol 1 g of benzyl ester of hyaluronic acid, 5% esterified, (HYAFF®11) (2.47 millimoles) with a mean molecular weight of 200 Kda, is solubilised in 50 ml of water. The solution is cooled to –1° C. and then 40 mg of TEMPO (0.26 millimoles) and 260 mg of sodium bromide (2.5 millimoles) are added in that order. A solution of 15% sodium hypochlorite is added in a quantity of 0.89 ml, equal to 1.852 millimoles, corresponding to 75% of the moles present in HYAFF®11. The solution is stirred and the pH maintained at 9-9.2 by adding a solution of 0.5 molar NaOH. Some minutes later, the pH will become stabilised without any further addition of 0.5 M NaOH. A volume of 5 ml of absolute ethanol is added and the solution is neutralised to pH 6.9-7.2 by adding 1 molar HCl. Subsequently, 95 mg of sodium borohydride is added and the mixture is stirred overnight at room temperature. The solution is neutralised to pH 6 once more and precipitated with acetone.

The product is characterised analytically to determine the percentage of percarboxylation.

Yield from the reaction: 90%

Percentage of percarboxylation (acidimetric): 75%

EXAMPLE 10

Preparation of 50% percarboxylated hyaluronic acid, starting from an ester derivative of hyaluronic acid with 50% esterified benzyl alcohol 1 g of benzyl ester of 50% esterified hyaluronic acid, (HYAFF®11) (2.30 millimoles) with a mean molecular weight of 200 Kda, is solubilised in 50 ml of water. The solution is cooled to –1° C. and 40 mg of TEMPO (0.26 millimoles) and 260 mg of sodium bromide (2.5 millimoles) are added in that order. A solution of 15% sodium hypochloride is added in a quantity of 0.552 ml, equal to 1.150 millimoles, corresponding to 50% of the moles present in HYAFF 11. The solution is stirred and the pH maintained at 9-9.2 by adding a solution of 0.5 M NaOH. Some minutes later the pH becomes stabilised without any further addition of the solution of 0.5 M NaOH. A volume of 5 ml of absolute ethanol is added and the solution is neutralised to a pH of 6.9-7.2 by adding 1 M HCl. Subsequently, 95 milligrams of sodium borohydride is added, and the mixture is stirred overnight at room temperature. The solution is neutralised again to a pH of 6 and precipitated with acetone.

The product thus obtained is characterised analytically to determine the percentage of percarboxylation.

Yield from the reaction: 90%

Percentage of percarboxylation (acidimetric): 50%

EXAMPLE 11

Preparation of 50% percarboxylated hyaluronic acid, starting from a sulphated hyaluronic acid with a degree of sulphation of 3

1 g of sulphated hyaluronic acid with a degree of sulphation of 3 (1.41 millimoles) and a mean molecular weight of 200 Kda, is solubilised in 20 ml of water. The solution is cooled to –1° C. and then 23 mg of TEMPO (0.15 millimoles) and 156 mg of Sodium bromide (1.5 millimoles) are added in that order. A solution of 15% sodium hypochloride is added in a quantity of 0.340 ml equal to 0.705 millimoles, corresponding to 50% of the moles present in HA sulphated to a degree of 3. The solution is stirred and the pH maintained at 9-9.2 by adding a solution of 0.5 molar NaOH. Some minutes later the pH becomes stabilised without any further addition of 0.5 molar NaOH solution. A volume of 5 millilitres of absolute ethanol is added and the solution is neutralised to a pH of 6.9-7.2 by adding 1 molar HCl. Subsequently, 95 milligrams of sodium borohydride is added, and the mixture is stirred overnight at room temperature. The solution is neutralised again to a pH of 6 and precipitated with acetone.

The product thus obtained is characterised analytically to determine the percentage of percarboxylation.
Yield from the reaction: 90%
Percentage of percarboxylation (acidimetric): 50%

EXAMPLE 12

Preparation of 75% percarboxylated hyaluronic acid, starting from an amide derivative of hyaluronic acid with dodecyl amine (HYADD®) with a degree of amidation of 5%

1 g of dodecyl amide of hyaluronic acid (HYADD®) at 5% (2.44 millimoles) with a mean molecular weight of 200 Kda, is solubilised in 100 ml of water. The solution is cooled to −1° C. and 40 mg of TEMPO (0.26 millimoles) and 260 mg of sodium bromide (2.5 millimoles) are added in that order. A solution of 15% sodium hypochloride is added in a quantity of 0.88 ml equal to 1.83 millimoles, corresponding to 75% of the moles present in HYADD® 3 5%. The solution is stirred and the pH maintained at 9-9.2 by adding a solution of NaOH 0.5 M. Some minutes later the pH becomes stabilised without any further addition of 0.5 M NaOH solution. A volume of 5 ml of absolute ethanol is added and the solution is neutralised to a pH of 6.9-7.2 by adding 1 molar HCl. Subsequently, 95 mg of sodium borohydride is added, and the mixture is stirred overnight at room temperature. The solution is neutralised again to a pH of 6 and precipitated with acetone.

The product thus obtained is characterised analytically to determine the percentage of percarboxylation.
Yield from the reaction: 90%
Percentage of percarboxylation (acidimetric): 75%

EXAMPLE 13

Preparation of 50% percarboxylated hyaluronic acid, starting from an amide derivative of hyaluronic acid with hexadecyl amine (HYADD®) with a degree of amidation of 3%

1 g of hexadecyl amide of hyaluronic acid (HYADD®) at 3% (2.45 millimoles) with a mean molecular weight of 200 Kda, is solubilised in 100 ml of water. The solution is cooled to −1° C. and 40 mg of TEMPO (0.26 millimoles) and 260 milligrams of Sodium bromide (2.5 millimoles) are added in that order. A solution of 15% sodium hypochloride is added in a quantity of 0.590 ml equal to 1.225 millimoles, corresponding to 50% of the moles present in HYADD® 4 3%. The solution is stirred and the pH maintained at 9-9.2 by adding a solution of NaOH 0.5 M. Some minutes later, the pH becomes stabilised without any further addition of 0.5 M NaOH solution. A volume of 5 ml of absolute ethanol is added and the solution is neutralised to a pH of 6.9-7.2 by adding 1 M HCl. Subsequently, 95 mg of sodium borohydride is added, and the mixture is stirred overnight at room temperature. The solution is neutralised again to a pH of 6 and precipitated with acetone.

The product thus obtained is characterised analytically to determine the percentage of percarboxylation.
Yield from the reaction: 90%
Percentage of percarboxylation (acidimetric): 50%

EXAMPLE 14

Preparation of 75% percarboxylated hyaluronic acid, starting from an autocross-linked derivative of hyaluronic acid (ACP) with a degree of cross-linking of 10%

1 g of cross-linked hyaluronic acid with a degree of cross-linking of 10% (2.52 millimoles) and a mean molecular weight of 200 Kda, is solubilised in 100 ml of water. The solution is cooled to −1° C. and 40 mg of TEMPO (0.26 millimoles) and 260 mg of sodium bromide (2.5 millimoles) are added in that order. A solution of sodium hypochloride at 15% is added in a quantity of 0.91 ml equal to 1.89 millimoles, corresponding to 75% of the moles present in the cross-linked hyaluronic acid with a degree of cross-linking of 10%. The solution is stirred and the pH maintained at 9-9.2 by adding a solution of 0.5 M NaOH. Some minutes later, the pH becomes stabilised without any further addition of 0.5 M NaOH solution. A volume of 5 ml of absolute ethanol is added and the solution is neutralised to a pH of 6.9-7.2 by adding 1 M HCl. Subsequently, 95 mg of sodium borohydride is added, and the mixture is stirred overnight at room temperature.

The solution is neutralised again to a pH of 6 and precipitated with acetone.

The product thus obtained is characterised analytically to determine the percentage of percarboxylation.
Yield from the reaction: 85%
Percentage of percarboxylation (acidimetric): 75%

ANTIBACTERIAL ACTIVITY

The zinc salt of hyaluronic acid with 25% percarboxylation prepared as described in the above Example 7 has been assayed for its antibacterial (Gram-positive e Gram-negative) activity, and compared with the corresponding zinc salt of non-percarboxylated hyaluronic acid. The zinc salts in freeze-dried form are re-dissolved with distilled water and maintained at a temperature of 4° C. Before use, the zinc salts solutions are filtered through a Millipore 0.45 micron filter.

For the experiments a suspension of *Escherichia coli* ATCC 10536 in a physiological buffered saline solution (PBS) was used, having $N=2.8 \times 10^8$ cfu/ml, wherein N is the number of bacterial cells in the suspension, expressed as colony forming units (cfu) per ml.

Starting from the above said bacterial suspensions, serial dilutions are prepared; from each diluted solution two samples of 1 ml (x and x') are taken, seeded on Tryptic Soy Agar (TSA) plates, and incubated for 24 hours at 36° C.

After incubation, the bacterial colonies are counted so to obtain a "test suspension" having a concentration ranging from $1.5 \times 10^8$ and $5 \times 10^8$ cfu/ml.

The number of bacterial cells in 1 ml of the bacterial suspensions, expressed as cfu/ml, is calculated by the following formula:

$$cfu/ml = c / [d(n_1 + 0.1 n_2)]$$

wherein:
c is the number of colonies in the samples x and x'
$n_1$ is the number of plates for the first dilution ($n_1=2$)
$n_2$ is the number of plates for the second dilution ($n_2=2$)
d is the dilution grade ($10^6$).

The antibacterial activity of the two zinc salts solutions prepared as above said, has been evaluated after contacting them with the bacterial suspensions at different times, i.e. after 30, 60, 90 and 120 minutes, according to the following procedure:

1 ml of the bacterial suspension has been added to 9 ml of a solution prepared by dissolving the zinc salts under examination in PBS so to obtain a concentration of 2.05 mg/ml. The control is constituted by the bacterial suspension in PBS.

All mixtures are stirred and incubated for 30 minutes at 37° C. After the above said contact times, two samples a and a' respectively of 1 ml and 0.1 ml for each mixture are transferred onto TSA plates and incubated for 24 hours at 37° C.

Once the incubation time is over, the colonies are counted and the number Na of bacterial cells, expressed in cfu/ml, in the mixtures under examination is obtained by applying the following formula:

$$Na = c/(ndV)$$

wherein:
c is the number of colonies in the samples a and a'
n is the total number of plates for the different dilutions
d is the dilution grade ($10^1$).
V is the volume of the sample (1 ml).

Once Na values are available for the mixtures under examination, the antibacterial activity is calculated according to the following formula:

$$R = (N\ 10^{-1})/Na$$

wherein:
N (cfu/ml) is the number of bacterial cells in the initial test suspensions;
Na (cfu/ml) is the number of bacterial cells in the mixtures under examination;
R is the decrease of bacterial vitality.

In the following Table 1 the results obtained for the antibacterial activity against *Escherichia coli* are summarised:

TABLE 1

| | | Na (cfu/ml) and R after contact times (min) | | | |
|---|---|---|---|---|---|
| Tested product | N (cfu/ml) | 30 | 60 | 90 | 120 |
| hyaluronic acid Zn salt (comparative product) | $2.8\ 10^8$ | Na = $1.5\ 10^6$ R > $10^1$ | Na = $1.5\ 10^5$ R > $10^2$ | Na = $1.5\ 10^4$ R > $10^3$ | Na = $1.5\ 10^3$ R > $10^4$ |
| percarboxylated hyaluronic acid Zn salt (product of invention) | $2.8\ 10^8$ | Na = $1.5\ 10^4$ R > $10^3$ | Na = $1.5\ 10^3$ R > $10^4$ | Na = $1.5\ 10^2$ R > $10^5$ | Na = $1.5\ 10^1$ R > $10^6$ |

The essential requirement for a substance to be considered as bactericide is that this substance reduces the initial bacterial charge of at least 5 logarithmic units (i.e. R>$10^5$). The above results indicate therefore that the zinc salt of percarboxylated hyaluronic acid of the invention has a higher antibacterial activity than the corresponding salt of hyaluronic acid not percarboxylated, so that it can be considered as bactericide whereas the not percarboxylated product cannot be.

EVALUATION OF THE MINIMUM INHIBITORY CONCENTRATION (MIC)

The MIC value is the minimum concentration of an antibacterial substance able to prevent turbidity of a bacterial suspension. The two zinc salts under examination are tested by broth microdilution, to evaluate the corresponding MIC values.

A total volume of 2 ml are used for the dilution.

Dilution of the Antimicrobial Agent (Zinc Salt)

The percarboxylated hyaluronic acid zinc salt of the invention and the hyaluronic aci dzinc salt as comparative product are diluted in 1 ml of Müller Hinton broth (MH broth) having a concentration twice higher than the desired concentration, given that the addition of inoculum (i.e. the bacterial suspension) causes a 1:2 dilution of the initial concentration.

11 tubes are prepared having concentrations from 2 μg/ml to 2048 μg/ml, and a control tube containing only the bacterial suspension.

Preparation of the Inoculum 4-5 colonies of *Escherichia coli* ATCC 10536 coming from a culture of 24 hours on non selective agar plates, are suspended directly in broth so to obtain a turbidity of 0.5 Mc Farland (approximately $1 \cdot 10^8$ cfu/ml).

The so prepared suspension is then diluted to 1:100 in MH broth so to obtain a bacterial concentration of $1 \cdot 10^6$ cfu/ml. 1 ml of this diluted suspension is added to each tube containing 1 ml of the substance under examination diluted in MH broth, thus obtaining a final inoculum of $5 \cdot 10^5$ cfu/ml.

Incubation

The tubes are incubated in an oxygen thermostat at 35° C. for 16-20 hours before evaluating the MIC values.

Results

All testing tubes containing the not percarboxylated hyaluronic acid salt showed turbidity, whereas the tube containing the percarboxylated hyaluronic acid zinc salt of the invention in concentration of 2.048 mg/ml.

In conclusion, the above experiment has proved that the not percarboxylated hyaluronic acid salt does not posses any bactericidal activity against *Escherichia coli*, whereas the percarboxylated hyaluronic acid of the invention possesses antibacterial activity and has a MIC of 2.048 mg/ml.

The invention claimed is:

1. Percarboxylated polysaccharides, wherein the polysaccharide is selected from the group consisting of hyaluronic acid derivatives, having a "percarboxylation degree" between 1% and 100%, wherein the term "percarboxylation degree" means the percentage of carboxy groups or modifications thereof introduced by an oxidation process of the primary hydroxyl groups present on the said polysaccharides, said hyaluronic acid derivatives comprising at least one repeating unit of formula (I):

(I)

[Chemical structure: disaccharide repeating unit with substituents $R_1$, $R_2O$, $OR_3$, $OR_4$, ROC, NHR$_5$]

wherein R is OH, O$^-$, or an alcoholic or amino group of the aliphatic, aromatic, arylaliphatic, cycloaliphatic, or heterocyclic series;
$R_1$ is COR$_6$,
$R_6$ is (i) OH, O$^-$, an alcoholic or amino group of the aliphatic, aromatic, arylaliphatic, cycloaliphatic, or heterocyclic series;
(ii) an alcoholic group of hyaluronic acid, or
(iii) an amino group of N-deacetylated hyaluronic acid;
$R_2$, $R_3$, $R_4$, equal or different from each other, are H, SO$_3^-$, an acyl group deriving from a carboxylic acid of the aliphatic, aromatic, arylaliphatic, cycloaliphatic, or heterocyclic series; or a residue of hemiester of succinic acid or of heavy metal salts of hemiester of succinic acid; and $R_5$ is $COCH_3$, H, $SO_3^-$, an acyl group deriving from a carboxylic acid of the aliphatic, aromatic, arylaliphatic, cycloaliphatic, or heterocyclic series, or an acyl group of hyaluronic acid;

provided that, when R is OH or $O^-$, $R_5$ is $COCH_3$ and $R_2=R_3=R_4=H$, $R_6$ is different from OH and $O^-$.

2. Percarboxylated polysaccharides according to claim 1, wherein the said percarboxylation degree is between 25% and 75%.

3. Percarboxylated polysaccharides according to claim 1, further salified with metals of the $4^{th}$, $5^{th}$, or $6^{th}$ period of the periodic table of elements.

4. Percarboxylated polysaccharides according to claim 3, wherein the said metals are selected from the group consisting of silver, cobalt, iron, copper, zinc, arsenic, strontium, zirconium, antimony, gold, caesium, tungsten, selenium, platinum, gallium, ruthenium, bismuth, tin, titanium and mercury.

5. A pharmaceutical composition comprising as the active agent at least one percarboxylated polysaccharide of claim 3, alone or in combination with biologically or pharmacologically active substances, in combination with pharmaceutically acceptable excipients and/or diluents.

6. The pharmaceutical composition according to claim 5, wherein the said pharmacologically active substances are selected from the group consisting of antibiotics, anti-infective, antimicrobial, antiviral, antifungal, cytostatic, anticancer, anti-inflammatory, wound healing agents, anaesthetics, cholinergic or adrenergic agonists and antagonists, antithrombotics, anticoagulants, haemostatics, fibrinolytics, and thrombolytics.

7. The pharmaceutical composition according to claim 5, wherein the said biologically active substances are selected from the group consisting of proteins and their fragments, peptides and polynucleotides, growth factors, enzymes, vaccines and substances used in the treatment of diseases associated with genetic defects, deforming and hereditary diseases.

8. A pharmaceutical composition comprising as the active agent at least one percarboxylated polysaccharide of claim 1, alone or in combination with biologically or pharmacologically active substances, in combination with pharmaceutically acceptable excipients and/or diluents.

9. The pharmaceutical composition according to claim 8, wherein the said pharmacologically active substances are selected from the group consisting of antibiotics, anti-infective, antimicrobial, antiviral, antifungal, cytostatic, anticancer, anti-inflammatory, wound healing agents, anaesthetics, cholinergic or adrenergic agonists and antagonists, antithrombotics, anticoagulants, haemostatics, fibrinolytics, and thrombolytics.

10. The pharmaceutical composition according to claim 8, wherein the said biologically active substances are selected from the group consisting of proteins and their fragments, peptides and polynucleotides, growth factors, enzymes, vaccines and substances used in the treatment of diseases associated with genetic defects, deforming and hereditary diseases.

11. A composition comprising a percarboxylated polysaccharide according to claim 1.

12. The composition of claim 11, wherein the composition further comprises a biomaterial, which comprises said percarboxylated polysaccharide, optionally being in combination with biologically or pharmacologically active substances.

13. The composition of claim 12, wherein the biomaterial is in the form of a scaffold for cell cultures.

14. The composition of claim 12, wherein the biomaterial is in the form of a filler in plastic-aesthetic surgery.

15. The composition of claim 12, wherein the biomaterial is in the form of a substitute for the vitreous humor.

16. The composition of claim 11, wherein the composition further comprises a surgical glue, which comprises fibrin and said percarboxylated polysaccharide.

* * * * *